US012788969B2

(12) United States Patent
Palanker et al.

(10) Patent No.: US 12,788,969 B2
(45) Date of Patent: Nov. 10, 2026

(54) HONEYCOMB-SHAPED ELECTRO-NEURAL INTERFACE FOR RETINAL PROSTHESIS

(71) Applicant: The Board of Trustees of the Leland Stanford Junior University, Stanford, CA (US)

(72) Inventors: Daniel V. Palanker, Sunnyvale, CA (US); Thomas Flores, San Francisco, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 131 days.

(21) Appl. No.: 18/990,235

(22) Filed: Dec. 20, 2024

(65) Prior Publication Data

US 2025/0121181 A1 Apr. 17, 2025

Related U.S. Application Data

(62) Division of application No. 17/438,807, filed as application No. PCT/US2020/024619 on Mar. 25, 2020, now abandoned.

(60) Provisional application No. 62/823,395, filed on Mar. 25, 2019.

(51) Int. Cl.
*A61N 1/05* (2006.01)
*A61N 1/36* (2006.01)

(52) U.S. Cl.
CPC ....... *A61N 1/0543* (2013.01); *A61N 1/36046* (2013.01); *A61N 1/3616* (2013.01)

(58) Field of Classification Search
CPC . A61N 1/0543; A61N 1/36046; A61N 1/3616
See application file for complete search history.

(56) References Cited

U.S. PATENT DOCUMENTS 11,497,913 B1 * 11/2022 Shire .................. A61N 1/36046

* cited by examiner

*Primary Examiner* — Eugene T Wu
(74) *Attorney, Agent, or Firm* — LUMEN PATENT FIRM

(57) ABSTRACT

We provide a 3-dimensional configuration of an electrode array for neural cell stimulation designed to leverage migration of retinal cells into voids in the subretinal space. Walls surrounding each pixel align the electric field vertically, matching the orientation of bipolar cells in the retina, and thereby reduce the stimulation threshold. These walls also decouple the field penetration depth from the pixel width, enabling a decrease of the pixel size down to cellular dimensions. Inner retinal cells migrate into the electrode cavities, which enables very efficient stimulation. Due to 1-dimensional alignment of electric field along the cavities, stimulation threshold current density does not increase significantly with the reduced pixel size, unlike the quadratic increase seen with planar arrays.

9 Claims, 6 Drawing Sheets

HONEYCOMB-SHAPED ELECTRO-NEURAL INTERFACE FOR RETINAL PROSTHESIS

GOVERNMENT SPONSORSHIP

This invention was made with Government support under contract EY027786 awarded by the National Institutes of Health. The Government has certain rights in the invention.

FIELD OF THE INVENTION

This invention relates to electrical stimulation of neural cells.

BACKGROUND

Conventional stimulation arrays for visual prostheses have a planar configuration of active and return electrodes. This planar configuration creates severe difficulties in scaling the prostheses to have sufficiently small and densely packed pixels to provide useful visual acuity. There are two main difficulties as pixel size is reduced: increased crosstalk between adjacent pixels and an increase in pixel stimulation threshold (i.e., the current density required to obtain a cellular response). The increase of stimulation threshold as pixel size decreases is particularly troublesome, since the required current density becomes biologically unsafe at desirable pixel sizes for retinal implants. Accordingly, it would be an advance in the art to alleviate these limitations of planar stimulation arrays.

SUMMARY

We provide a novel 3-dimensional configuration of an electrode array designed to leverage migration of retinal cells into voids in the subretinal space. Walls surrounding each pixel align the electric field vertically, matching the orientation of bipolar cells in the retina, and thereby reduce the stimulation threshold. These walls also decouple the field penetration depth from the pixel width, enabling a decrease of the pixel size down to cellular dimensions. Inner retinal cells migrate into the honeycomb wells, so that these neurons reside within the electrode cavities, which enable very efficient stimulation. Due to 1-dimensional alignment of electric field along the vertical walls of the honeycomb cavities, stimulation threshold current density does not increase significantly with the reduced pixel size, unlike the quadratic increase with planar arrays. This 3-D electrode configuration may enable restoration of sight with much smaller pixels and hence higher acuity than with planar electrode arrays. Similar 3-D arrays could be used for electro-neural interfaces with the brain in other applications.

In preferred embodiments, the pixel cavities have depths between 10 μm and 100 μm, and widths between 5 μm and 100 μm. The current density at the active central electrodes is preferably between 0.01 $A/cm^2$ and 1 $A/cm^2$. The width of the apparatus as a whole is preferably between 0.5 mm to 5 mm, making it suitable for retinal implantation. The charge injection per pulse on the active electrodes is preferably between 0.1 $mC/cm^2$ and 10 $mC/cm^2$.

Applications include retinal prostheses for restoration of sight in retinal degeneration, and high-resolution electro-neural interfaces in general. This work advantageously enables scaling the pixels in electro-neural interfaces down to cellular dimensions.

DETAILED DESCRIPTION

Section A describes general principles relating to embodiments of the invention. Section B provides a detailed experimental example.

A) General Principles

Figure 1:
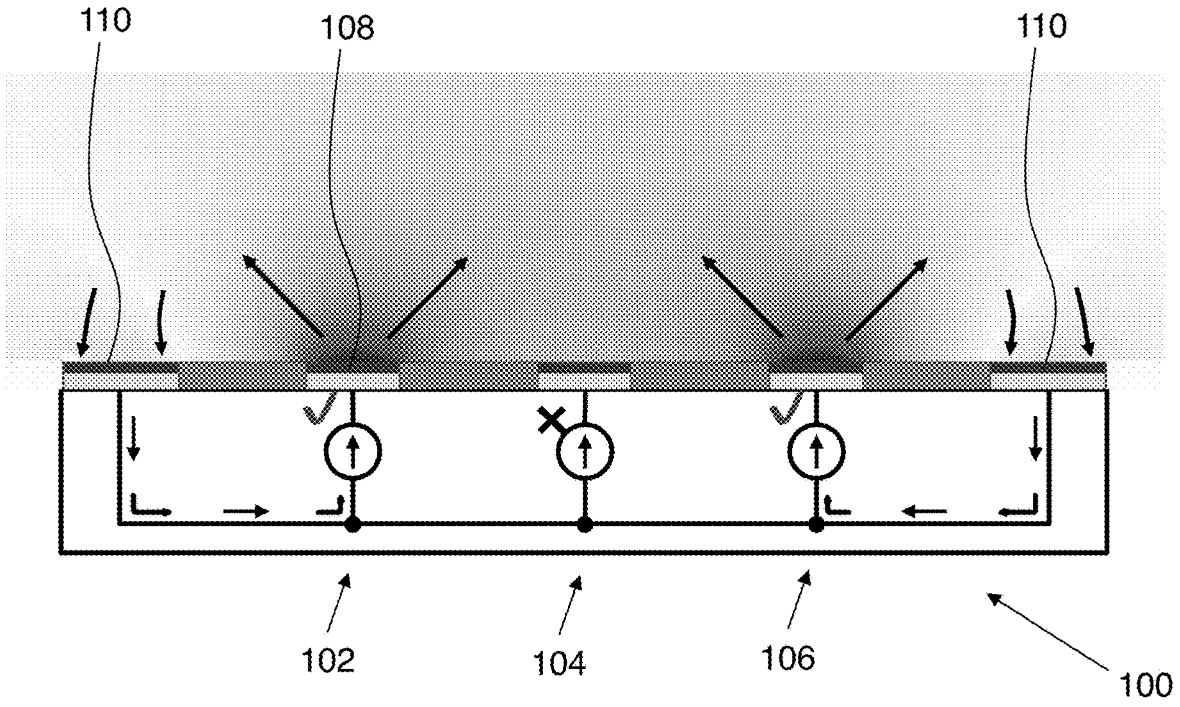
FIG. 1 (prior art)
FIG. 1 schematically shows operation of a planar array for neural cell stimulation.

To better appreciate embodiments of the invention, it is helpful to first consider operation of a conventional planar stimulation array 100, as shown on FIG. 1. This is a cross section view of a row of pixels 102, 104, 106. The "ON" pixels (102 and 106, also marked with a check) generate electric current and inject it into the electrolyte through the central active electrode (e.g. 108 of pixel 102), which is then collected by the remote return electrode 110 outside the pixels (or between the pixels). Current flow is shown with black arrows. Current flow through the electrolyte creates a gradient of electric potential (shading). Current spreads from the active electrodes in all directions, affecting cells in the neighboring pixels as well. E.g., "OFF" pixel 104, marked with an X, will receive parasitic stimulation from neighboring pixels, undesirably resulting in low contrast.

Figure 2A:
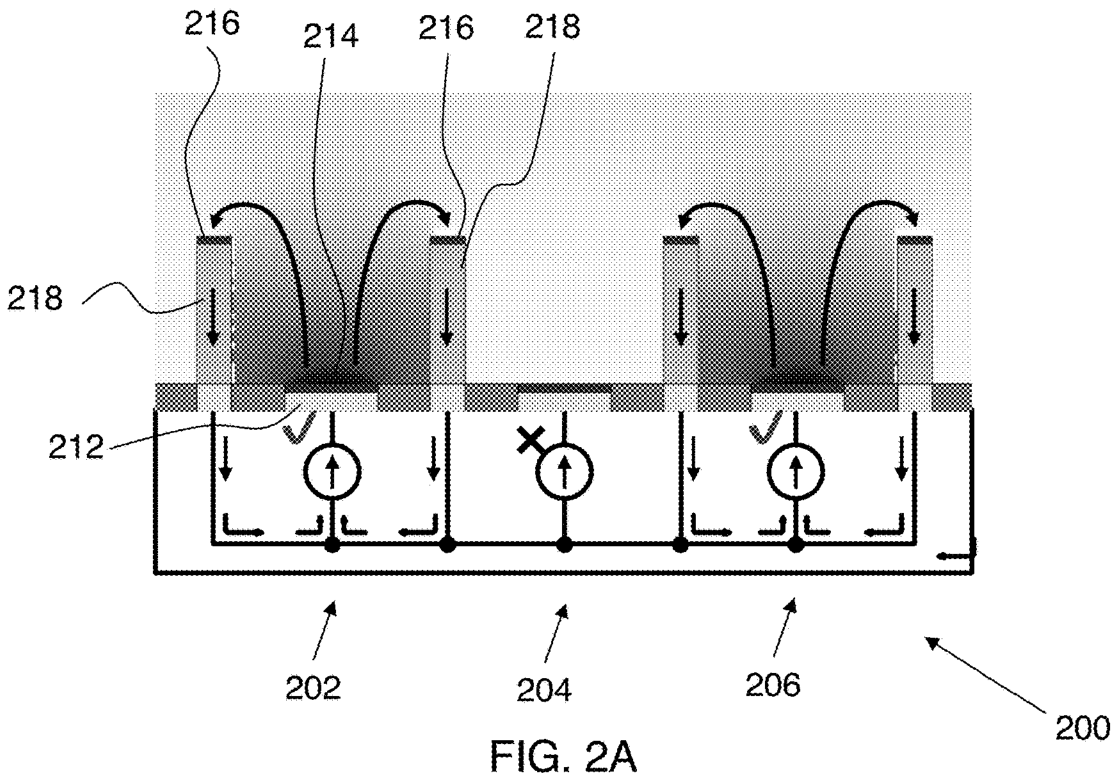
FIG. 2A shows a first embodiment of the invention.

FIG. 2A shows a cross section of a first embodiment of the invention. Here stimulation array 200 includes pixels 202, 204, 206. "ON" pixels 202 and 206 (check mark) generate electric current and inject it into the electrolyte through the central active electrode (e.g., 214 of pixel 202). Current flows up through the electrolyte (tissue) and is collected by the return electrode 216 on top of the walls 218 to complete the circuit. Flow through electrolyte creates a gradient of electric potential (shading) primarily in front of the "ON" pixels, allowing for localized stimulation of the retina. Note the reduced shading above pixel 204 on FIG. 2A compared to pixel 104 on FIG. 1. High-capacitance material 216 deposited on top of the conductive honeycomb wall 218 ensures that a majority of the current through the electrolyte is collected at the top of the walls, and a negligible amount of current is collected through the sides of the conductive walls due to low capacitance of the interface between metal and electrolyte. Such a configuration enables manufacturing of the elevated return electrodes in a honeycomb structure without the need for sidewall passivation or insulation.

More precisely, a first embodiment of the invention is apparatus for electrical stimulation of neural cells including an array of cavities configured to allow migration of neural cells inside the cavities. Each cavity has a floor (e.g., 212 on FIG. 2A) and electrically conductive walls (e.g., 218 on FIG. 2A). Each cavity has a first electrode (e.g., 214 on FIG. 2A)

disposed on its floor and has a second electrode (e.g., 216 on FIG. 2A) disposed on top of its walls and vertically separated from its corresponding floor electrode. During operation of the apparatus, an ionic current flows through contents of the cavities. A per-cavity capacitance of the second electrodes is greater than a per-cavity capacitance of the conductive walls, whereby the second electrodes preferentially collect the ionic current relative to sides of the conductive walls. Preferably, the capacitance per unit area of the second electrodes is at least 100× greater than the capacitance per unit area of the conductive walls.

Figure 2B:
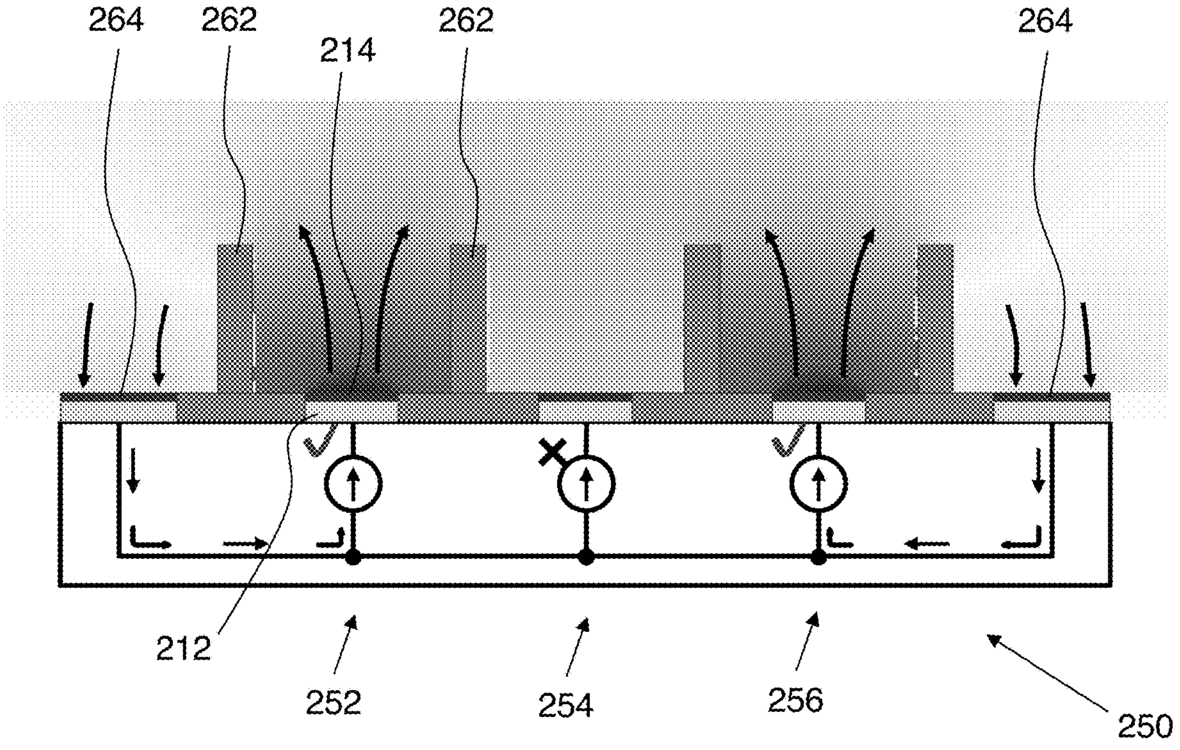
FIG. 2B shows a second embodiment of the invention.

FIG. 2B shows a cross-section view of a second embodiment of the invention. Here stimulation array 250 includes pixels 252, 254, 256. "ON" pixels 252 and 256 (check mark) generate electric current and inject into the electrolyte through the central active electrode (e.g., 214 of pixel 252). Current flows up through the honeycomb well surrounded by electrically insulating walls 262 and then is collected by the remote return electrode 264 outside the pixels. Flow through the electrolyte creates a gradient of electric potential (shading) primarily in front of the "ON" pixels, allowing for much better localized stimulation of the retina than would be present without the vertical walls. Note the reduced shading above pixel 254 on FIG. 2B compared to pixel 104 on FIG. 1.

More precisely, a second embodiment of the invention is apparatus for electrical stimulation of neural cells including an array of cavities configured to allow migration of neural cells inside the cavities. Each cavity has a floor (e.g., 212 on FIG. 2B) and electrically insulating walls (e.g., 262 on FIG. 2B). Each cavity has a first electrode (e.g., 214 on FIG. 2B) disposed on its floor. The apparatus includes a common return electrode (e.g., 264 on FIG. 2B) disposed outside the array of cavities. During operation of the apparatus, an ionic current flows through contents of the cavities. The electrically insulating walls improve stimulation efficiency and reduce cross-talk between neighboring cavities of the apparatus by forcing the ionic current to travel vertically within the cavities.

Preferred configurations for the embodiments of FIGS. 2A-B are as follows. The depth of the cavities is preferably between 10 μm and 100 μm. The width of the cavities is preferably between 5 μm and 100 μm. The depth of the cavities is preferably greater than the width of the cavities. The array of cavities is preferably periodic, and in this case it is preferred that the cavities be hexagonal. In preferred embodiments, the neural cells are retinal cells. Preferably, an injected charge density at first electrodes of the cavities is between 0.1 $mC/cm^2$ and 10 $mC/cm^2$ in operation.

In the preceding description it has been convenient to refer to the cavities as each having walls. However, in an array structure (e.g., as on FIG. 4A) it is apparent that walls are shared between adjacent cavities in most cases. For any shared wall, the assigning of parts of the wall to the two adjacent cavities is arbitrary. Practice of the invention does not depend at all on how this theoretical division is considered to be done. Similarly, local return electrodes (e.g., 216 on FIG. 2A) are similarly shared between adjacent cavities in most cases. For any shared return electrode, the assigning of parts of the return electrode to the two adjacent cavities is arbitrary. Practice of the invention does not depend at all on how this theoretical division is considered to be done.

B) Detailed Experimental Example

B1) Introduction

Electronic approaches to restoration of sight are rapidly advancing, with some systems approved for clinical use in patients blinded by inherited retinal degeneration (retinitis pigmentosa, RP), and a few others in clinical trials. Patients affected by RP and implanted with the epiretinal prosthesis Argus II (Second Sight Medical Products, Inc, Sylmar, CA) or the subretinal Alpha IMS/AMS (Retina Implant AG, Reutlingen, Germany) demonstrated improved performance in ambulation and visual search, with the best reported visual acuities of 20/1260 and 20/546, respectively. Although encouraging, those benefits are not sufficient to help with the most prevalent form of retinal degeneration, age-related macular degeneration (AMD), where patients lose high-resolution central vision but retain peripheral field with acuity typically no worse than 20/400.

Visual acuity of 20/200, the limit of legal blindness in the United States, geometrically corresponds to a pixel pitch of about 50 μm. Safe charge injection across the electrode-electrolyte interface limits the minimum size of the electrode. In addition, cross-talk between neighboring electrodes increases with decreasing pixel size. The latter issue can be addressed by providing a circumferential return electrode in each pixel, but this approach further reduces penetration depth of electric field into tissue.

The electrode-tissue separation in subretinal space can be reduced using pillar electrodes. Migration of the retinal cells of the inner nuclear layer (INL) to fill the voids in such a 3-D implant brings the target neurons closer to the stimulating electrodes, thereby reducing the stimulation threshold. However, such pillar electrodes decreased the stimulation threshold only by a factor of two and did not enable significant reduction of the pixel size below 55 μm. The fundamental problem limiting the electrode size is the shape of the electric field expanding from a small electrode and returning to another electrode under the target cells.

Figure 3A:
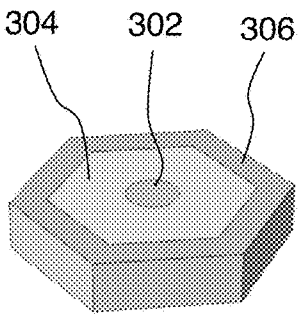
FIGS. 3A-B are another view of the difference between planar and non-planar stimulation arrays.

Here, we present a novel 3-D geometry for a subretinal prosthesis, which we call the honeycomb configuration, to overcome these limitations and enable scaling the pixels down to cellular dimensions. In this approach, return electrodes are elevated on vertical insulating walls surrounding each pixel, which align the electric field vertically, matching the orientation of bipolar cells in the retina, and thereby reducing the stimulation threshold. Compare elevated return electrode 306 on FIG. 3B to the planar configuration of FIG. 3A. Here 302 is the stimulation electrode and 304 is the substrate on which stimulation electrode 302 is disposed.

Figure 3B:
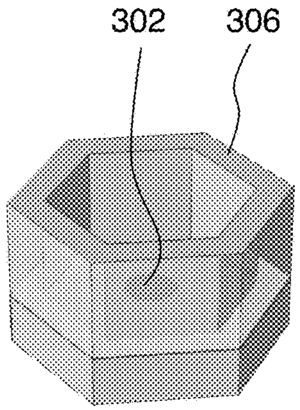
Figure 3C:
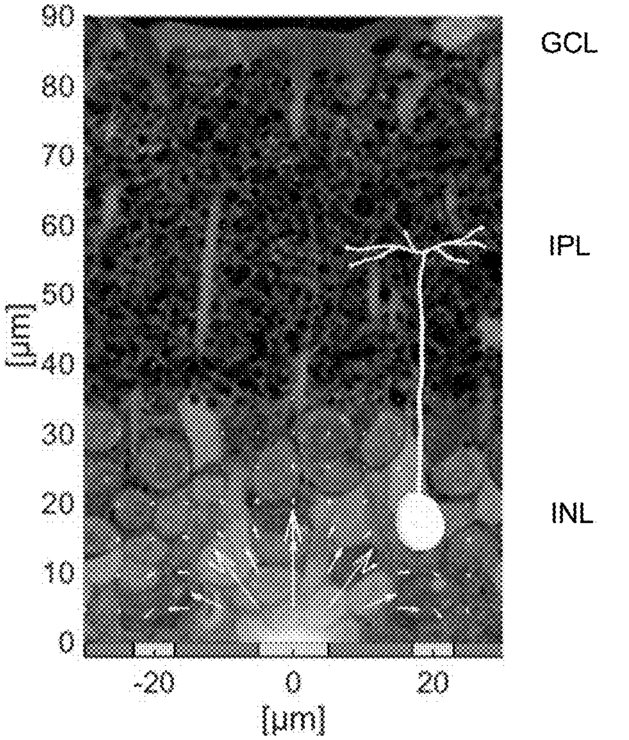
FIGS. 3C-D show overlay of the implants depicted in FIGS. 3A-B with retinal anatomy.
Figure 3D:
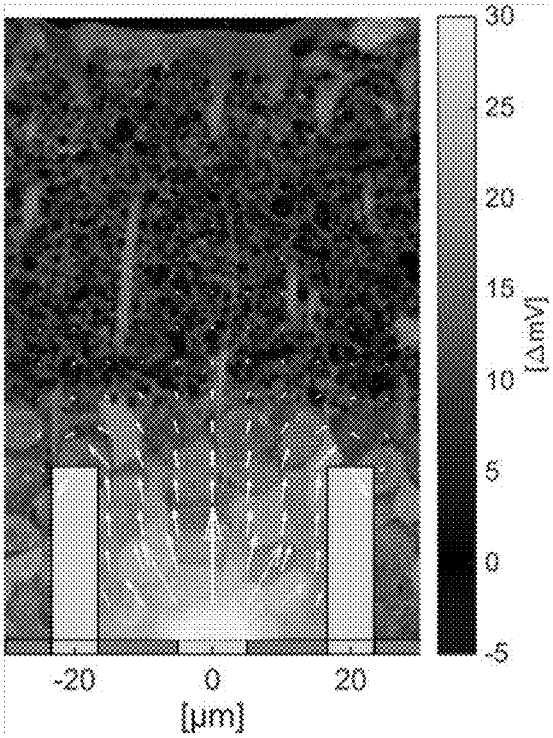

FIG. 3C shows that planar pixels with circumferential returns generate locally confined electric fields with shallow vertical penetration. Cells in electric field polarize according to the potential difference across their length. Bipolar cell somas and axon terminals reside in the INL (inner nuclear layer) and IPL (inner plexiform layer), respectively. Electric potential is therefore represented with respect to potential in the middle of IPL. FIG. 3D shows that return electrodes on top of insulating walls create a vertical dipole confined to the local pixel volume and thereby maximize the vertical potential drop across the target cell layer. Current magnitude (arrow length) is shown in log scale. Potential difference with respect to the middle of IPL (57 μm) is shown in gray scale for 68 nA current.

These walls also decouple the field penetration depth from the pixel width, enabling a decrease of the pixel size down to cellular dimensions. We first study the anatomical integration of such 3-D structures with the retina using implants with 20, 30 and 40 μm pixels, and then quantify the electrical stimulation capabilities using a network-mediated retinal stimulation model validated by experimental measurements. Our results indicate that such technology opens the door to prosthetic vision with acuity better than 20/100, which would be highly beneficial not only for patients completely blinded by RP, but also for restoration of central vision in the much larger population of patients with AMD.

In the past, we described the migration of the retinal cells into the apertures in a membrane implanted in the subretinal space, and its implications for subretinal prosthesis. However, in that configuration, the bottom of the implant had openings allowing electric current to propagate below the implant. In reality though, the retinal prosthetic implants are typically solid, i.e. electric current does not penetrate through them, and hence it can flow only upward, as shown in FIGS. 3C-D here. Therefore, we describe here a different geometry and materials of the return electrodes suitable for optimal shaping of electric field with such stimulating arrays.

B2) Results

B2a) Anatomical Integration

Figure 4A:
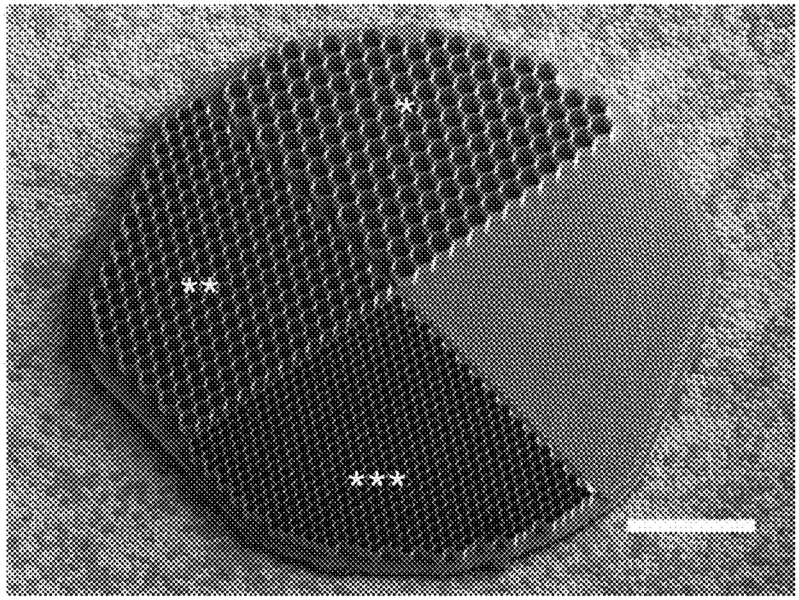
FIGS. 4A-B show images of a fabricated array of cavities.
Figure 4B:
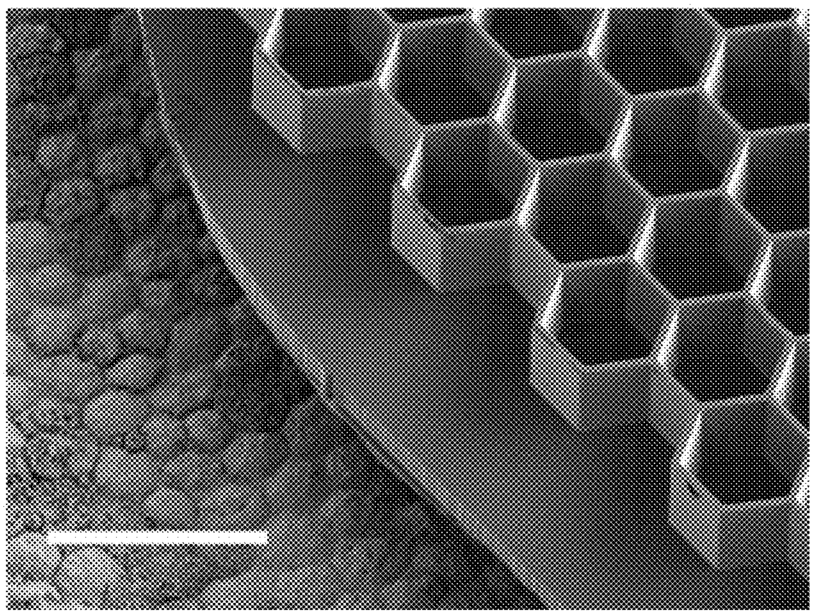
Figure 4C:
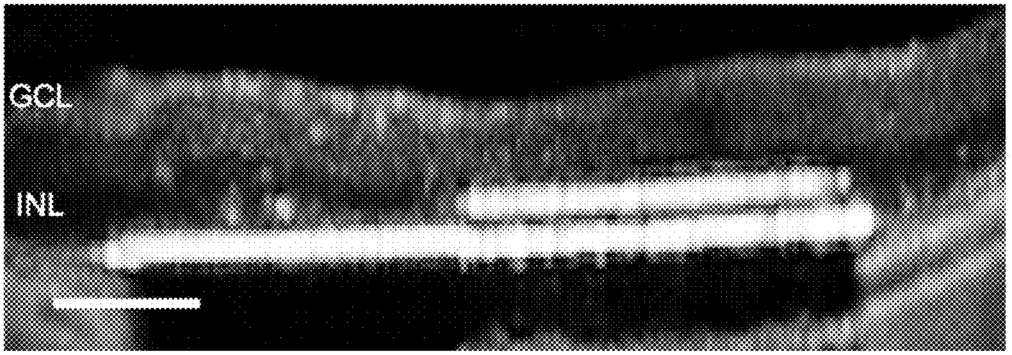
FIG. 4C shows an image of the honeycomb implant under the animal retina.

FIGS. 4A-C show subretinal honeycomb implants. FIG. 4A shows an image of a 1 mm wide device with 25 μm deep honeycombs of 40 (*), 30 (), and 20 μm (*) pixel pitch. The fourth quadrant contained a 10 μm pitch structure, which was beyond the processing limit and hence did not develop. We refer to it as the "flat" region due to the absence of walls. FIG. 4B is a higher magnification of the honeycombs with 30 μm pitch. FIG. 4C is an OCT image of the subretinal implant in RCS rat 6 weeks post-op. Scale bars are 200 μm for FIG. 4A, 50 μm for FIG. 4B, and 100 μm for FIG. 4C.

To assess integration of the honeycombs with the degenerate retina, silicon arrays of 1 mm in diameter were implanted into the subretinal space of RCS rats (P180-300, n=6) for 6 weeks. Each array was divided into quadrants containing honeycombs with 40, 30, and 20 μm pitch and a flat area (FIG. 4A). Arrays were fabricated in silicon using a Bosch etching process to define the 25 μm deep honeycomb chambers (FIG. 4B). Implant integration with the retina was monitored in-vivo by optical coherence tomography (OCT) (FIG. 4C). Six weeks after implantation, the INL is barely detectable by OCT above the honeycombs (FIG. 4C, right) but visible above the flat quadrant (FIG. 4C, left) and outside the implant, indicating INL migration into the cavities.

Figure 5:
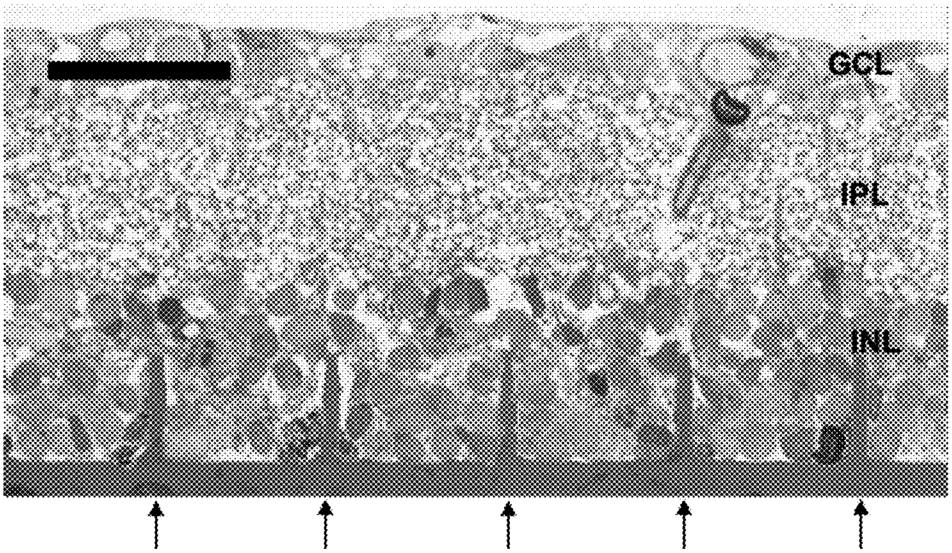
FIG. 5 shows histology of the retina integrated with an implanted honeycomb array.

Histology confirmed migration of the INL cells, showing no visible signs of fibrosis or trauma, as shown on FIG. 5. The retinal structure remains preserved, with clearly defined INL, inner plexiform layer (IPL), and ganglion cell layer (GCL). Although some of the INL cells remain above the honeycomb walls, cavities are completely filled with the densely packed cells down to the base of the array. Black arrows point at the location of the original walls, which were removed after the sample embedding and refilled with epoxy for sectioning. The scale bar on FIG. 5 is 40 μm.

Comprehensive assessment of the retinal integration and immune response was performed using 3-D confocal imaging of the whole-mount retina with the implant. 3-D reconstruction reveals dense packing of the INL (DAPI) in most of observed honeycomb cavities. Side views through single honeycomb rows demonstrate complete migration down to the base of the arrays.

Within the degenerate RCS control retina, extended microglial processes within the IPL indicate the microglial resting state, while microglia below the INL extend their processes through the degenerate outer plexiform layer (OPL). With the subretinal implants, microglia in the IPL appear similar to those in the control retina, with extended processes indicating the microglial resting state. With a planar implant, microglia reside close to the device surface. Presence of the cortical response with these active implants indicates that microglia on a subretinal prosthesis does not prevent electrical stimulation. With the honeycomb implant, microglia processes extend primarily along the top of the walls, with minimal extension into the wells.

The extent of retinal integration was assessed by analyzing cell density as a function of height from the base in the cavities of each size. An average of 508, 45% and 54% of the INL cells were found inside the cavities with honeycomb pitch of 40, 30 and 20 μm, respectively. Since the electric field can extend above the walls (FIG. 6A), more cells can be stimulated.

B2b) Modeling Retinal Response In-Vivo

Figure 6A:
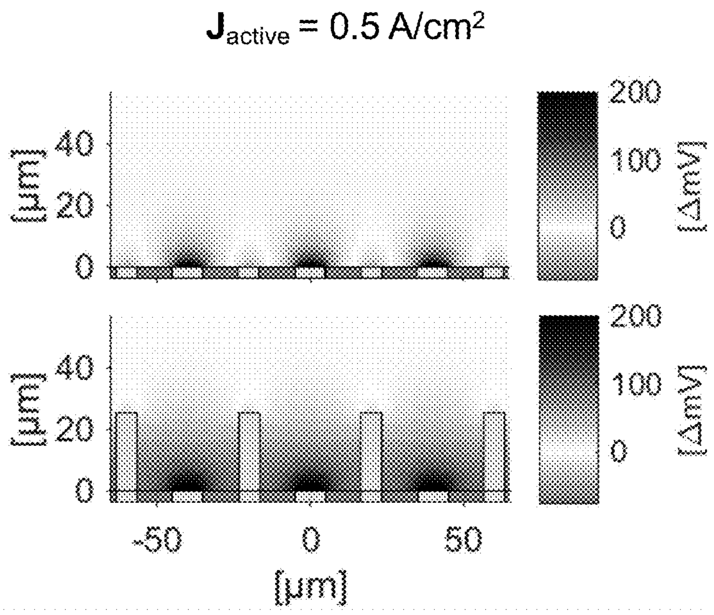
FIG. 6A shows simulated electric potential for planar (top) and honeycomb (bottom) arrays.
Figure 6B:
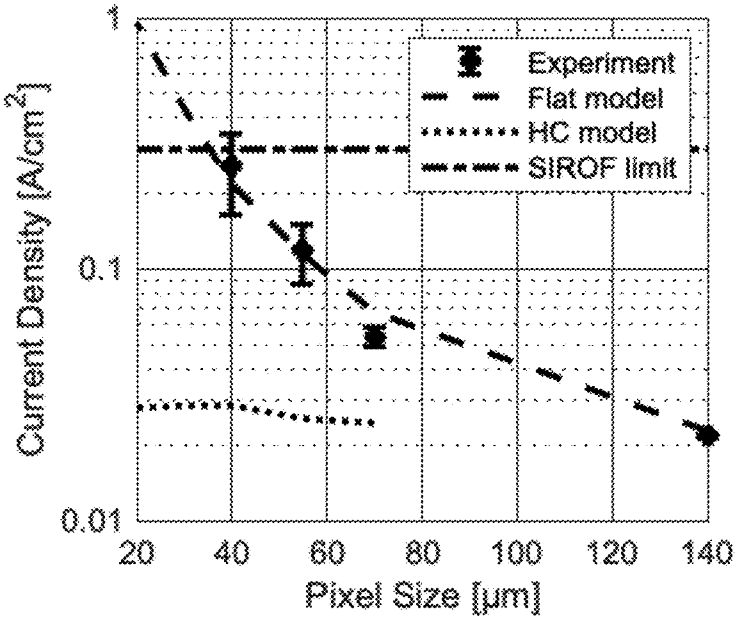
FIG. 6B shows experimental and simulated threshold current density vs. pixel size for a planar array, compared to the safety limit and compared to simulated threshold current density vs. pixel size for a honeycomb array.

FIG. 6A shows electric potential for planar (top) and honeycomb (bottom) arrays with respect to middle of IPL (z=57 μm), calculated for active electrode current density of 0.5 A/cm$^2$. FIG. 6B shows experimental thresholds (data points) and calculated thresholds for planar (dashed line) and honeycomb (dotted line) devices in terms of current density on active electrode. The planar models (both binary and linear, as described below) reproduce the trend observed in experimental measurements. Honeycomb arrays significantly reduce the stimulation threshold (dotted line), enabling safe operation of devices with pixels below 40 μm. The maximum charge injection by SIROF (3 mC/cm$^2$ for a 10 ms pulse) is shown with a dash-dotted line. Here SIROF is short for Sputtered IRidium Oxide Film. Any other bio-compatible high-capacitance material can also be used for the high capacitance electrodes, such as IrOx deposited by different means (electroplating, chemical deposition etc.), porous Pt, PEDOT, carbon nanotubes, etc.

To assess the benefits of the honeycomb-shaped arrays, we used a model of network-mediated retinal stimulation. To validate this model, we first compared the modeling results with the in-vivo stimulation thresholds measured in rats having planar subretinal photovoltaic implants with various pixel sizes, and then computed the stimulation thresholds for honeycombs of various sizes.

Complete modeling of this system would require converting the simulated electric field produced by the device (FIG. 6A) into the response of the inner retinal neurons, applying subsequent network-mediated processing to RGC activity, and finally translating the retinal output into the cortical visually evoked potentials (VEP)—an immensely complex modeling task with multiple unknowns. This task can be simplified with the following assumptions: (1) network-mediated stimulation elicits RGC activity that follows a sigmoidal curve, and (2) cortical response is driven by summation of the retinal signals and also follows a sigmoidal curve. We approximated the sigmoidal dependence of the network-mediated retinal response on electric field from previous experiments by two extremes: (1) a step function modeling a binary transition across the stimulation threshold and (2) a linear function modeling a gradual increase in the neural output in response to increasing stimulus. Consequently, the total retinal response is calculated by integrating the cellular responses over the volume of INL with either (1) a binary coefficient, i.e. calculating just the fraction of the INL volume above the stimulation threshold, or (2) with cellular response proportional to its polarization. We will therefore refer to the two models as "binary" and "linear", respectively.

Electric field in the retina was calculated using a finite element model of the entire arrays in COMSOL Multiphysics 5.0, using the electrostatics module to solve Maxwell's equations for electric potential, assuming steady-state electric currents. Computed fields were then converted into the retinal response using both the binary and linear models. Each model had only one fitting parameter for relating its retinal output to amplitude of the cortical response. For a binary model, it was the fraction of the INL cells which should be activated to elicit a cortical response, while for a linear model it was the slope of the linear fit. Irradiance is converted into current density based on the pixel geometry and light-to-current conversion efficiency of our 2-diode pixels. To fit the binary model, we therefore compute the electric field vs irradiance and calculate the percent of the INL above the stimulation threshold (4.8 mV for 10 ms anodic pulse, see Methods) for all pixel sizes. Using our previously recorded experimental thresholds for 140, 70, 55, and 40 μm pixels, we see that to elicit VEP response, 8.27±1.42% of the INL volume should be above the stimulation threshold. Both binary and linear models yield a very similar scaling of the stimulation threshold with the pixel size, indicating that the critically important factor is the shape of the electric field, rather than the details of the sigmoidal response curve.

B2c) Stimulation Thresholds with Honeycomb Arrays

Using the binary model parameters verified by comparison with the in-vivo stimulation thresholds obtained with planar implants, we calculated the stimulation thresholds for honeycomb arrays (see details in Methods). These thresholds, in terms of the current density on the active electrode for a 10 ms pulse, are significantly lower than with planar pixels of the same size, and do not increase much with decreasing pixel size (FIG. 6B). Planar arrays with circumferential returns suffer from a rapid decline of the electric potential along the vertical axis due to (a) the radial spread of electric field from the active electrode and (b) the coplanar return electrode (FIG. 3C). As a result, planar pixels smaller than 40 μm require current density greater than the safe charge injection limit of SIROF for a 10 ms pulse (>30 mA/cm$^2$ or charge density of >3 mC/cm$^2$). Placement of the return electrode on top of the insulating honeycomb walls surrounding the pixel forces the current to flow primarily upward from the active electrode (FIG. 3D), thereby greatly increasing the depth at which the electric potential exceeds the stimulation threshold. In addition, with honeycomb arrays, penetration depth of the electric field into tissue is set by the height of the walls, and hence is decoupled from the pixel width. Therefore, the stimulation threshold in terms of current density does not depend on the pixel width (FIG. 6B), enabling scaling the pixels down to the size limited only by the retinal migration, i.e. by cellular dimensions. Improvements in the stimulation threshold are summarized in Table 1.

TABLE 1

Computed stimulation threshold current densities for different pixel sizes. Asterisks indicate current densities for a 10 ms pulse which exceed the SIROF charge injection limit.

| Pixel Size (μm) | Planar Threshold (A/cm$^2$) | Honeycomb Threshold (A/cm$^2$) | Threshold Reduction Factor Planar/Honeycomb |
|---|---|---|---|
| 70 | 0.064 | 0.024 | 2.70 |
| 55 | 0.11 | 0.025 | 4.28 |
| 40 | 0.21 | 0.028 | 7.44 |
| 30 | 0.43* | 0.028 | 15.2 |
| 20 | 0.94* | 0.028 | 33.3 |

In addition to stimulation thresholds, honeycomb electrodes significantly improve the spatial selectivity of electrical stimulation (i.e. the contrast between adjacent pixels), which is essential for high-acuity vision. To replicate the grating patterns used for in-vivo assessment of visual acuity, we simulate the electric field distribution from our arrays with alternating rows of ON and OFF pixels. For electrodes of both configurations, increasing current density leads to an increase in positive potential above the ON pixels, as well as negative potential above the OFF pixels. Insulating walls of the honeycomb prevent the lateral spread of the electric field and thereby widen the dynamic range of selective activation of the ON pixels. Further, electric field extends above the walls of the honeycomb to stimulate cells up to 40 μm from the base of the cavity within the safe charge injection limits, allowing for up to 99% activation of the total inner retina without crosstalk.

B3) Discussion

Our study provides a path toward improvement in spatial resolution of retinal prostheses far beyond the limits of the current systems. Until recently, the best acuity of prosthetic vision achieved in clinical testing was 20/546, observed in 2 patients with the Alpha IMS/AMS subretinal implants [2,20]. With 70 μm pixels, this prosthesis is underperforming by a factor of 2 with respect to its sampling limit, leading some to conclude that continued reduction in pixel size will not improve visual acuity. However, the bottleneck for these devices may be electrical rather than biological: the monopolar configuration of this implant, with active electrodes in each pixel sharing a common remote return electrode, results in a strong cross-talk between neighboring electrodes, greatly reducing spatial contrast. An alternative design that provides active and return electrodes in each pixel improves the localization of electric field and associated spatial resolution. Indeed, a recent clinical trial with photovoltaic subretinal implants having 100 μm pixels with local return electrodes demonstrated visual acuity up to 20/460—only 15% below the sampling limit with this pixel size (20/400). Moreover, in rats, similar implants with 70 μm and 55 μm pixels provided grating acuity also matching the sampling limit. This demonstrates that visual acuity can reach the sampling density limit of the stimulating array if it properly confines the electric field in each pixel. However, further decrease in the pixel size is limited by the rapid increase of the stimulation threshold, which rises close to the safety limit with flat pixels of 40 μm width (FIG. 6B).

The radically different geometry of the stimulating array described in this work—the honeycomb configuration—addresses this fundamental limitation. Current from the active electrode at the bottom of the cavity flows upwards due to confinement of the pixel by insulating walls (FIGS.

3B and 3D). This change in the shape of the electric field dramatically reduces the stimulation threshold. Moreover, one-directional flow of electric current radically changes the scaling of the stimulation threshold with the pixel size. In spherical geometry, an electrode smaller than the distance to target cells can be approximated as a point source. Since the required current does not change with the electrode size in this case, the current density increases inversely proportional to the electrode area, i.e. quadratic with its radius. If the ratio of the electrode size to pixel width is maintained, smaller pixels will require higher current densities, which are limited by the material properties. With one-dimensional flow of current, however, the situation is different: the current density required for a certain potential drop does not change with the pixel width, and therefore pixels can be made much smaller while retaining the same current density on the electrodes. For photovoltaic pixels it means that the threshold irradiance should remain nearly the same for all pixel sizes, as long as the relative dimensions of electrodes to pixel width do not change.

The honeycomb design is uniquely suited for subretinal placement due to the ability of the inner retinal neurons to migrate into voids in the subretinal space. Our study demonstrates that the inner retinal neurons readily migrate into wells as small as 18 μm in width (20 μm pixel pitch). Tissue viability after 6 weeks demonstrates that diffusion of oxygen and nutrients from the retinal vasculature located above the implant is sufficient for the cell survival within 25 μm high walls. Since no lower bound of integration was observed in our study, pixel width may continue to scale down, but certainly not below the cell size of about 10 μm. Determination of the exact minimum within this range will require further experimentation. Even without any further decrease in the pixel size, arrays with 20 μm pixels should enable spatial resolution matching the natural acuity in rats, and acuity better than 20/100 in humans.

Migration of the majority of the INL into the cavities does not seem to affect the rest of the retinal structure, with clearly delineated INL, IPL, and GCL. Since all the connections of the INL cells to RGCs are located above the honeycomb walls in the IPL, we expect that the retinal signal processing will not be affected by this migration. Lateral connectivity between bipolar cells via horizonal cells connected to terminals of photoreceptors in the outer plexiform layer (OPL) is likely missing in the degenerate retina due to absence of photoreceptors. The number of microglia at the honeycomb walls was found to be similar to that with planar devices, and since the latter elicit VEP throughout the life of the animals, immune response with both implants appears to be acceptable. Interestingly, with honeycombs, microglia are localized to the upper portion of the walls, allowing neurons to migrate closer to the stimulating electrode.

Existing subretinal prostheses with a distant return electrode can also incorporate the vertical walls around pixels. In such a monopolar configuration, polarization of bipolar cells migrating into the wells should become more efficient due to vertical alignment of electric field, and hence the stimulation thresholds as well as the cross-talk between neighboring pixels should decrease, as illustrated in FIG. 2B. However, without local returns, electric potential inside the dark pixels will still be affected by its illuminated neighbors, and so the dynamic range of the patterns presented on such array will be lower than with the bipolar electrode configuration, shown in FIG. 2A.

In a steady state, current density on electrode surface is proportional to its capacitance per unit area. Therefore, if an electrode is composed of two materials having very different capacitance, current will flow predominantly to the one with higher capacitance. This phenomenon enables fabrication of the vertical walls of the 3-D electrodes from a conductive material, as long as its capacitance is much lower than that of the material deposited on top of the walls for return electrode. Even though the walls are made of a conductive material, they attract very little current in electrolyte and hence behave in a liquid as if they are made of an insulator because their capacitance per unit area is very low. For example, the walls can be electroplated from gold, having capacitance on the order of 0.01 $mF/cm^2$ in saline, while the return electrode on top of the walls can be made of Iridium Oxide, having capacitance of 1-10 $mF/cm^2$. Due to conductive nature of the walls made from metal, the Irox on top of such walls can be electroplated.

Alternatively, IrOx can be deposited by sputtering, but conductive walls will connect this coating to the electrical circuit on the surface of the device. Walls can be made from other metals, including platinum, aluminum, molybdenum, and others.

Side walls can also be coated with a non-conductive material to prevent any current between the electrolyte and the side walls. For example, oxidation of aluminum or molybdenum makes its surface non-conductive. Walls may also be insulated by additive processes, including, but not limited to, atomic layer deposition or photolithography of non-conductive materials. Alternatively, they can be made of an insulator. In this case, the return electrode deposited on top of such a wall should be connected to the electrical circuit via conductive tracks deposited for this purpose on top of the walls.

Pixels in the implant can be photovoltaic, i.e. convert light falling onto them into electric current using photodiodes connected between the active and return electrodes. Alternatively, electric current can be delivered to the electrodes via wired connections.

To allow cellular migration into the honeycomb cavities, their width should exceed the cell size, i.e. be wider than 5 micrometers. The benefit of the cavities becomes negligible when their widths significantly exceeds their depth. As shown in FIG. 6B, for retinal stimulation, it becomes negligible with pixels larger than 100 micrometers. To be used for subretinal implantation, i.e. to enable convenient tiling of the rigid arrays to follow the curved surface of the human eye, the size of the array should be in the range of 0.5 to 5 mm, and more typically 1-3 mm. At these dimensions, the array does not require the use of flexible materials as previously claimed, however larger arrays may incorporate a flexible substrate to conform to the eye. The depth of the cavities should be such that it allows migration of the cells from the inner nuclear layer, i.e. approximately the thickness of the inner nuclear layer plus the subretinal debris layer, i.e. in the range of 20-70 micrometers. Tissue viability after 6 weeks implantation in-vivo indicates that perforations at the bottom of the wells are not required for additional nutrient flow and for tissue survival.

Sidewalls can be designed to enable explantation of the implant while simultaneously improving mechanical stability within the subretinal space. Completely smooth, vertical walls, as shown in this study, should not exert much mechanical force on the tissue when the device is removed from the tissue. However, tissue migrating into the cavities provides a means to anchor the device laterally with respect to the retina. Additional overhang at the top of the wall can be introduced by electroplating above the trench guiding the electroplating procedure. In this case the cavity opening $d_o<d_c$ becomes smaller than its width, and hence the implant stability along the z axis can be further improved. This may, however, may make explantation of the device more traumatic, and so the exact configuration can be decided based upon patient's age and likelihood of the explantation.

As shown in Table 1, stimulation thresholds are in the range of 0.01-1 A/$cm^2$, with 10 ms pulse duration. Therefore, electrode material should be selected such that it can inject charge density in the range of 0.1-10 mC/$cm^2$.

Reflective side walls of the honeycombs can help direct the radiation to the light-sensitive area of the implant at the bottom of the wells, if the implant is tilted relative to the incoming light. For this purpose, walls made of metal using electroplating are advantageous due to high reflectivity of metals to visible and infrared light. Other materials and coatings with high reflectivity can also be used for this purpose, especially for light incident at the walls at nearly grazing angles.

B4) Methods

B4a) Passive Honeycomb Implants

Passive honeycomb implants were fabricated from crystalline silicon wafers using two mask layers to generate patterns for deep silicon etching. A hexamethyldisilazane (HMDS) primed wafer was spin-coated with 2 μm of negative photoresist (AZ5214-IR) and processed to define the honeycomb walls. This resist was further treated with UV for 15 min to enhance the selectivity during the subsequent etch. 25 μm deep cavities were formed in the exposed silicon regions using a Bosch etch process. After the honeycomb-defining resist was removed, photoresist (7.5% SPR 220-7, 68% MEK, and 24.5% PGMEA) was spray-coated over the wafer to a thickness of 14 μm and processed to define the releasing trenches around the 1 mm wide arrays. A second Bosch process was applied to create these releasing trenches, after which the photoresist was removed. The wafer was spray-coated with a protective 60 μm thick photoresist, and subsequently underwent backside grinding (Grinding and Dicing Services, Inc., San Jose, CA, USA) from 500 to 50 μm in thickness from the base of the honeycombs. Subsequent etching of the remaining excess silicon in $XeF_2$ gas completed the release of the implants. The resulting structures are shown in FIGS. 4A-B. Cavities are arranged in a hexagonal honeycomb patterns of 40, 30 and 20 μm pitch, having 25 μm high walls of 4, 3, and 2 μm thicknesses, respectively, on a 10 μm thick base. The fourth quadrant was designed for honeycombs of 10 μm pitch, but these were beyond the processing limit for our lithography system and did not develop. We refer to this region as the "flat" quadrant in the text. A 50 nm thick oxide was grown on the silicon implant's surface to prevent its dissolution in-vivo.

B4b) Animals and Surgical Procedure

All experimental procedures were conducted in accordance with the institutional guidelines and the ARVO Statement for the Use of Animals in Ophthalmic and Vision Research. Animal care and subsequent implantations were conducted using rats with retinal degeneration from a Royal College of Surgeons (RCS) colony maintained at the Stanford Animal Facility. N=6 animals were implanted with honeycomb arrays, with implantations occurring between P180 and P300 to ensure complete degeneration of the photoreceptors. Animals were anesthetized with a mixture of ketamine (75 mg/kg) and xylazine (5 mg/kg) injected intramuscularly. A 1.5 mm incision was made through the sclera and choroid 1.5 mm posterior to the limbus. The retina was lifted with an injection of saline solution, and the implant was inserted into the subretinal space. The conjunctiva was sutured with nylon 10-0, and topical antibiotic (bacitracin/polymyxin B) was applied on the eye postoperatively. Surgical success and retinal reattachment were verified using Optical Coherence Tomography (OCT) (HRA2-Spectralis; Heidelberg Engineering, Heidelberg, Germany). The animals were euthanized 6 weeks after implantation. Additional animals for a control group had flat active implants, and were sacrificed after about 6-months long in-vivo studies.

B4c) Whole-Mount Retinal Imaging

Animals were euthanized with an intracardiac injection of Beuthanesia, and eyes were enucleated and rinsed in phosphate buffered saline (PBS, Gibco; Thermo Fisher Scientific, Sunnyvale, CA, USA). Anterior segment and lens were removed, and upon locating the implant under a stereo microscope, the eye cup was cut to a 3 mm×3 mm square centered around the implant, and fixed in 4% paraformaldehyde (PFA; EMS, PA, USA) for 12 hours at 4° C. The implant was kept in place to prevent tissue damage or reorganization due to its removal. Samples were permeabilized with 1% Triton X-100 (Sigma-Aldrich, CA, USA) in PBS for 3 hours at room temperature. The samples were put in 10% bovine serum albumin (BSA) blocking buffer for 1 hour at room temperature, followed by a 12 hour incubation at room temperature with two primary antibodies; rabbit anti-IBA1 (1:200; Wako Chemicals, VA, USA) and mouse anti-Glutamine Synthetase (GS, 1:100; Novus Biologicals, CO, USA) in 0.5% Triton X-100, 5% BSA in PBS. Samples were washed for 6 hours at room temperature in 0.1% Triton X-100 in PBS (PBS-T) and incubated for 12 hours at room temperature with 2 secondary antibodies: donkey anti-rabbit Alexa Fluor 488 (1:200; Thermo Fisher Scientific, Sunnyvale, CA, USA) and donkey anti-mouse CY3 (1:200; Jackson ImmunoResearch Inc., PA, USA) and counterstained with 4', 6-Diamidin-2-phenylindol (DAPI) in PBS. After 6 hours of washing in PBST, the samples were mounted with Vectashield (H-1000; Vector Laboratories, Burlingame, CA, USA).

3-D imaging was performed using a Zeiss LSM 880 Confocal Inverted Microscope with Zeiss ZEN Black software. Image planes were acquired through the total thickness of the retina using a Z-stack, with upper and lower bounds defined at the inner limiting membrane (ILM) and 10 μm below the base of the honeycomb cavities, respectively. Stacks were acquired in the center of each honeycomb quadrant using a 40× oil-immersion objective with acquisition area >225 μm×225 μm, 360 nm z-step, and 0.55 μm pinhole.

B4d) Image Analysis

Confocal datasets were analyzed using the FiJi distribution of ImageJ. To analyze the cell density in the wells and above the implant, we first maximized the contrast in the individual XY planes to ensure 0.3% channel saturation to correct for brightness variations at different Z positions in the stack. The XY planes were then de-speckled, and background subtracted. A Gaussian blur filter ($\sigma$=3 pixels, 0.42 μm) was applied to smoothen brightness variations within individual cells. The XY planes were then passed through an edge detection filter, and the final image constructed from the background-subtracted OR combination of the processed and edge detected images. For cell density analysis, the channel threshold was adjusted (default method) to provide a binary representation of the cells. The density of cells in the XY plane, defined as the percent of the area occupied by cells, was then computed, taking into account the area occupied by the honeycomb walls. To account for local variations in retinal histology, each honeycomb unit was independently analyzed, with the cell density normalized to the maximum within the unit stack. The percent of INL contained within the cavities is calculated as $$\%_{INL} = \frac{\int_0^{z'} D(z)dz}{\int_0^{z''} D(z)dz} \cdot 100$$

where D(z) is the relative density of cells per XY plane as a function of height (z) from the base (z=0), z' is the wall height (25 μm), and z" is the end of INL, defined as a point where D(z)<0.02.

Six implanted devices, each containing 40, 30, and 20 μm sized honeycombs, were imaged and analyzed. In 3 devices, the 20 μm sized honeycombs were damaged, and so these were excluded from the analysis.

B4e) Histological Preparations

After confocal imaging, samples were rinsed in a buffer and fixed in 1.25% glutaraldehyde solution for 24 hours at room temperature. They were then post-fixed in osmium tetroxide for 2 hours at room temperature and dehydrated in graded alcohol and propylene oxide. Following overnight infiltration in epoxy (without DMP-30) at room temperature (Electron Microscopy Sciences-Araldite-EMbed, RT13940, Mollenhauer's kit), samples were left in an oven for 36 hours at 70° C. Epoxy blocks were then trimmed until the silicon implants were exposed. To prevent damage to the sectioning knife and formation of silicon debris from the honeycomb structure, the silicon implants were removed using a $XeF_2$ etch (Xactix e-1, 23° C., 3 Torr). Blocks were then refilled with epoxy and put in a vacuum desiccator for two hours, followed by overnight baking at 70° C. This refilling of the void left after etching of the implant provided structural support during sectioning. The 700 nm thick sections (cut by Reichart UltracutE) were stained with toluidine blue for light microscopy.

B4f) Modeling the Electric Field and Retinal Stimulation

Electric field in the retina was calculated using a 3-D finite element model of the complete array in COMSOL Multiphysics 5.0, using the electrostatics module to solve Maxwell's equations for electric potential, assuming steady-state electric currents. The modeled arrays are 1 mm in diameter, 30 μm thick, and are composed of hexagonal pixels of various sizes, listed in Table 2, with return electrodes connected into a single mesh.

TABLE 2

Number of pixels and their geometry in modeled photovoltaic arrays.

| Pixel Size [μm] | Number of Pixels | Active/pix [$\mu m^2$] | Return/pix [$\mu m^2$] |
|---|---|---|---|
| 140 | 37 | 1018 | 3823 |
| 70 | 157 | 254 | 1173 |
| 55 | 250 | 154 | 853 |
| 40 | 502 | 79 | 407 |
| 30 | 930 | 44 | 255 |
| 20 | 2172 | 20 | 112 |

The electric field is calculated in a volume (cube, side=10 mm) for which the ground (0 potential) is defined at the periphery. The modeled prosthesis functions as a closed system, in which all the current injected from active electrodes is collected on the return electrodes. Boundary conditions on electrode surfaces were defined as having a uniform current density, which corresponds to the steady state.

Current density on electrode-electrolyte interfaces in steady state is proportional to electrode capacitance per unit area. Therefore, current flows predominantly through the SIROF-coated top, even though the side walls are not insulated. For example, if SIROF coating is used as a return electrode material, its capacitance is about 1000 times higher than that of gold (10 mF/cm2 vs. 0.01 mF/cm2). The ratio of the area of the return electrode placed on top of the walls to the area of the side walls per pixel is equal to the ratio of the half-width of the wall to its height. With a wall having aspect ratio (height-to-width) of 5:1, the ratio of the areas of the top of the wall to its side is about 10:1. Therefore capacitance of the side walls will be 100 times smaller than that of the SIROF return electrode deposited on top of the honeycombs, per pixel. Hence, even though the walls are made out of metal, they will accept very low current in the electrolyte, and hence will act almost as if they have insulated side walls. This greatly simplifies fabrication of the honeycombs by allowing simple electroplating, without the need to insulate the side walls.

Two electrode configurations were studied: 1) planar with local returns (FIG. 3A) and 2) honeycomb with local returns (FIG. 3B). In both configurations, a common return electrode collects the current generated by all active pixels such that the total collected current is the sum of the injected currents on individual active electrodes. Side walls of the honeycombs are non-conductive. In our previous work with active devices, we assessed spatial resolution in-vivo by projecting grating patterns of various spatial frequencies with 100% contrast. The maximum resolution corresponds to activating alternating rows of pixels (ON or OFF rows). To replicate this configuration in simulations, we compute the electric field distribution using an identical activation scheme, and analyze the field at the center of the array, where the cross-talk between neighboring pixels is highest. To relate electrical simulations to light intensity with our photovoltaic prosthesis, the total current per pixel was calculated based on the diode area for the 2-diode configuration and measured light-to-current conversion efficiencies: 0.40, 0.31, 0.26, and 0.24 A/W for 140, 70, 55, and 40 μm pixels, respectively.

Retinal stimulation thresholds were evaluated using a model of network-mediated activation. In this approach, we assumed a network-mediated stimulation threshold being defined by a voltage drop across bipolar cells. In an external electric field, the intracellular medium becomes equipotential within a microsecond, resulting in hyperpolarization and depolarization of the cell membrane near and far from the anode, respectively. Using the retinal network-mediated stimulation threshold current density for large electrodes with 10 ms pulses from the literature, the average resistivity of the retina (1000 Ωcm), and a mean length of bipolar cells, estimated as the distance from the middle of INL to the middle of IPL (37 μm), we calculated a potential difference threshold of 4.8 mV from soma to axonal terminals for anodic stimulation. The cathodic threshold of −21 mV was calculated based on the network-mediated activation curve measured in rat retinas with anodic and cathodic stimulation, which was scaled to match the calculated anodic threshold.

It is important to note that our model is based on the stimulation current densities from the literature, while the calculated trans-cellular voltage scales linearly with the retinal resistivity, for which there is no consensus in the literature. We use the trans-cellular voltage only as a means for assessing the boundaries of the activation zone in tissue, relative to the stimulation threshold. Any variation in assumed retinal resistivity linearly affects the potential for the same current, including the threshold potential. Therefore, these variations do not affect the boundaries of the activation zone since they are calculated relative to the stimulation threshold.

We approximated the sigmoidal dependence of the network-mediated retinal response on increasing electric field from previous experiments by two extremes: (1) a step function modeling a binary transition across the stimulation threshold and (2) a linear function modeling a gradual increase in the neural output in response to increasing stimulus. Consequently, the total retinal response is calculated by integrating the cellular responses over the volume of INL with either (1) a binary coefficient, i.e. calculating just the fraction of the INL volume above the stimulation threshold, or (2) with cellular response proportional to its polarization.

The invention claimed is:

1. Apparatus for electrical stimulation of neural cells, the apparatus comprising:

an array of cavities configured to allow migration of neural cells inside the cavities;

wherein each cavity has a floor and electrically conductive walls;

wherein each cavity has a first electrode disposed on its floor;

wherein each cavity has a second electrode disposed on top of its walls and vertically separated from its corresponding floor electrode;

wherein during operation of the apparatus, an ionic current flows through contents of the cavities;

wherein a second electrode capacitance is greater than a conductive wall capacitance in each cavity, whereby the second electrodes preferentially collect the ionic current relative to sides of the conductive walls.

2. The apparatus of claim 1, wherein a depth of the cavities is between 10 μm and 100 μm.

3. The apparatus of claim 1, wherein a width of the cavities is between 5 μm and 100 μm.

4. The apparatus of claim 1 wherein a depth of the cavities is greater than a width of the cavities.

5. The apparatus of claim 1, wherein the array of cavities is periodic.

6. The apparatus of claim 5, wherein the cavities are hexagonal.

7. The apparatus of claim 1, wherein the neural cells are retinal cells.

8. The apparatus of claim 1, wherein an injected charge density at first electrodes of the cavities is between 0.1 $mC/cm^2$ and 10 $mC/cm^2$ in operation.

9. The apparatus of claim 1, wherein a capacitance per unit area of the second electrodes is at least 100× greater than a capacitance per unit area of the conductive walls.

* * * * *